US00PP07970P

United States Patent [19]

Bennett et al.

[11] Patent Number: Plant 7,970

[45] Date of Patent: Sep. 15, 1992

[54] MINIATURE ROSE PLANT NAMED 'LITTLE CAROL'

[76] Inventors: Cecilia L. D. Bennett, late of Chula Vista, by Susan O'Brien administrator; Susan M. O'Brien, deceased, 489 Minot Ave., Chula Vista, Calif. 91910, by Susan M. O'Brien administrator

[21] Appl. No.: 636,392

[22] Filed: Dec. 31, 1990

[51] Int. Cl.[5] ..... A01H 5/00

[52] U.S. Cl. ..... Plt./9

[58] Field of Search ..... Plt. 9, 10

*Primary Examiner*—James R. Feyrer

[57] ABSTRACT

The subject of the present disclosure is a new and distinct variety if miniature rose plant, named 'Little Carol', which is characterized by deep pink blooms ranging from near Magenta to near Rose Bengal. Blooms of this rose are usually borne one to a stem with hybrid tea form but on occasion may be produced in sprays of 3 to 5 or more. The bush is vigorous, well-branched and produces moderate to heavy quantity of blooms.

1 Drawing Sheet

The present invention relates to a new and distinct variety of a hardy, dwarf, bush plant of the miniature class; the variety being primarily characterized as deep pink.

The variety is further characterized by:

Long stemmed blooms of hybrid tea-type form, borne usually one to a stem but on occasion in sprays of 3 to 5 or more. The blooms are held very erect and well above the foliage.

The plant range in height from 18 to 24 inches (45 to 60 cm). The canes are sturdy and erect with moderate branching and medium to heavy foliage covering. The plant is a moderate to heavy bloomer that does well either in the greenhouse or outdoors.

The plant has good growth habits, well-shaped and attractive, bearing numerous leaflets of average size. I have found this variety to be easily asexually reproduced from cuttings.

The seed parent was Sonia (U.S. Plant Pat. No. 3,095), and the pollen parent was Jean Kenneally (U.S. Plant Pat. No. 5,637). It differs from its seed parent in the following ways. It is a miniature rose in deep pink, and Sonia is a grandiflora in pink blend. It differs from its pollen parent in the following ways. It produces deep pink flowers, and Jean Kenneally produces blooms in apricot blend.

The single color photographic view shows, in plan view, a bouquet of 'Little Carol' in various stages of maturity from bud stage to nearly open bloom stage.

The descriptive matter which follows pertains to roses grown and color values observed in plants and newly opened blooms in the months of March through November 1990. The plants were grown outdoors in Chula Vista, Calif., and are believed to be accurate standards for this cultivar in similar conditions of soil and climate elsewhere.

Referring now specifically to the new and distinct variety of miniature rose plant named 'Little Carol', the following is a detailed description thereof in outline; all major color plate identifications being by reference to the British Colour Council Horticultural Chart, except where common terms of color definition are employed.

Type: Hardy, dwarf, bushy, greenhouse or outdoor, exhibition or garden decorative potted plant.

Class; Miniature.

Variety name: Little Carol.

Flowers borne: Usually one to a stem, but occasionally in sprays of 3 to 5 or more on erect stems with foliage well below the blooms.

Quantity of bloom: Moderate to heavy both outdoors or greenhouse grown.

Bud:

*Peduncle.*—Average length (30 to 50 mm); average diameter and sturdy; ranging from near Scheeles Green (860/3 to 860/1 page 176) with occasional tinting of bronze.

*Hairs.*—Extremely small and sparse with a reddish color; located over the surface of the peduncle and calyx tube.

*Calyx.*—Color range same as peduncle.

*Opening.*—Opens well in all weather.

Bloom:

*Size when fully open.*—Average for a miniature variety (40 to 50 mm).

*Petalage.*—Very double — 35 to 40 petals, arranged regularly, plus 5 to 10 petaloids.

*Form.*—Urn-shaped to ovoid as the bloom opens. The petals remain somewhat cupped with the apex and/or margins reflexed outward, becoming at maturity more loosely cupped.

Petals: Fairly thick with good substance; both the upper and under surface of all petals have a matte finish.

*Shape.*—Outer petals are of a broad obovate form. The intermediate petals are very much like the outer petals only narrower. The inner petals are a broad lanceolate form; and the petaloids are also lanceolate with some occasional irregularities.

Color: Newly opened flowers from plants grown outdoors (March through November of 1990). Chula Vista, Calif.:

*All petals.*—Upper surfaces — Ranging from near Magenta (27/1 to 27 page 27) to near Rose Bengal (25/1 to 25 page 25) with a small base of near white. Under Surfaces — Slightly lighter tones of upper surfaces.

*General color effect.*—Newly opened flowers — Deep pink overall. Three days open — Slight fading of the outermost petals only. Three to five days open — Continued fading of outermost petals only.

*Flower longevity.*—(March through November 1990) Plant in pot 5 to 7 days from bud with sepals reflexed to fully open bloom. Holding at fully opened for 5 to 7 days longer. Cut bloom at living room temperature 10 to 14 days or longer.

Reproductive organs:

*Stamens.*—A generous amount arranged uniformly around the pistil.

*Filaments.*—Varying in length with shorter filaments more proximal to the pistil; pale yellow in color with anthers of golden yellow.

*Pollen.*—Abundant.

*Pistil.*—Short, spreading and abundant; pale yellow to reddish at the cap.

*Ovaries.*—All encased in calyx.

*Hips.*—Some.

*Seeds.*—3 to 5 more in each hip.

*Sepals.*—Permanent; spear-shaped; open as the bloom opens, recurving against the peduncle, when the bloom is fully opened. Occasional foliaceous appendages attractively supplement sepal terminals; these are of varying lengths.

Foliage:

*Leaves.*—5 to 7 leaflets on average; medium size for a miniature rose plant.

*Leaflets.*—Broad ovate-shaped.

*Margins.*—Very serrated with tinting of bronze, especially noticeable on the newer foliage.

*Color.*—Ranging from near Spinach Green (0960/3 to 0960 page 187) to near Scheeles Green (860/1 to 860 page 175) with occasional bronzing of the margins, especially on the newer foliage. Upper surfaces have a semi-glossy finish, and the under surfaces have a matte finish of a slightly lighter shade than the upper surfaces.

*Rachis.*—Medium strength; upper surface is grooved with very small hairs over the length of it. Under surface has few if any hairs but does contain 2 to 5 small thorns.

*Stipules.*—Varying in length from small to medium; average width; tapering auricles angled outward at about 45 degrees.

Growth:

*Habit.*—Dwarf, at 18 to 24 inches, average to bush; above average for a miniature rose plant.

*Rate and character.*—Vigorous and well-branched.

*Canes.*—Medium diameter; sturdy; held erect.

*Main stems.*—Color range same as foliage.

*Thorns.*—Averaging less than 5 to 10 per 10 cm on the main stems and branches. Reddish in color; average size; slender and hooked slightly downward.

*Branches.*—Coloration ranges the same as does that of the foliage.

The miniature rose plant and its flowers as herein described may vary in slight detail due to climate, soil and cultural conditions under which the variety may be grown; the presnt description being of the variety as grown in Chula Vista, Calif.

The following is claimed:

1. A new and distinct variety of miniature rose plant, named 'Little Carol', of hardy, dwarf, vigorous growth, well-branched and attractive in appearance, substantially as illustrated and described, characterized by its hybrid tea form blooms ranging from near Magenta to near Rose Bengal with flowers usually borne one to a stem but occasionally in sprays of 3 tO b 5 or more.

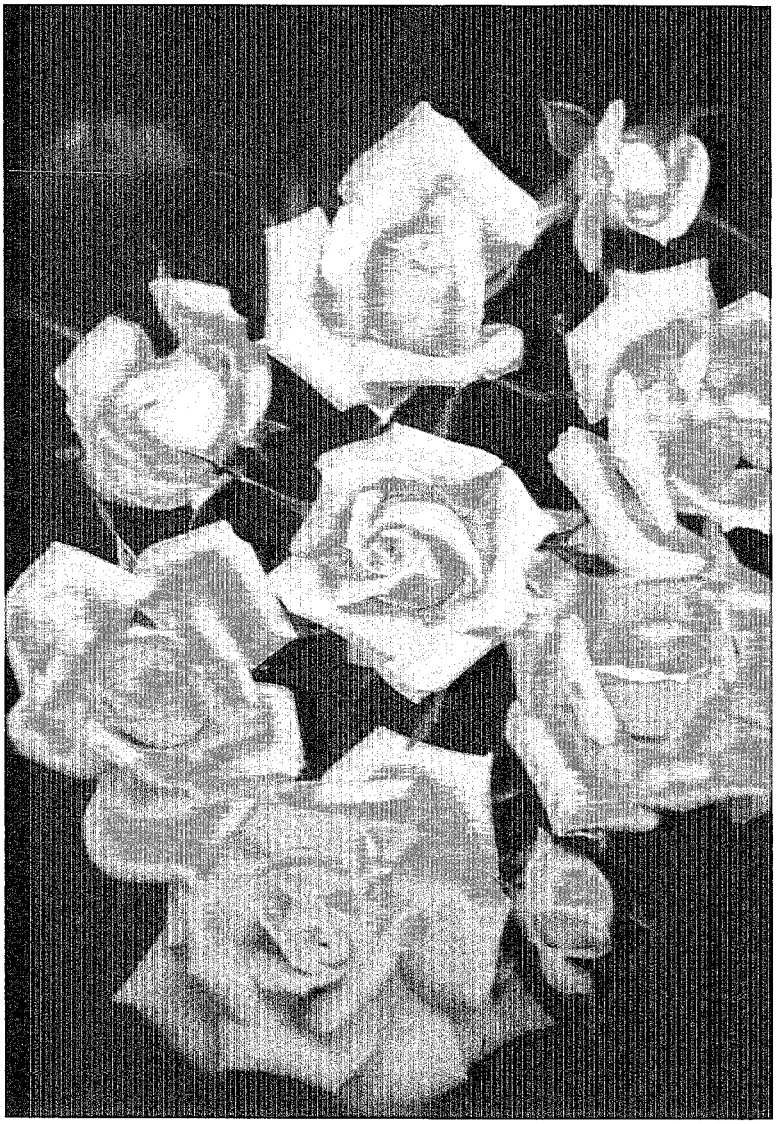

* * * * *